United States Patent [19]

Ross

[11] 4,402,580

[45] Sep. 6, 1983

[54] OPTICAL EXERCISING DEVICE

[76] Inventor: Richard Ross, 1708 Lee Rd., Winterpark, Fla. 32789

[21] Appl. No.: 173,957

[22] Filed: Jul. 31, 1980

[51] Int. Cl.³ .............................................. G03B 21/00
[52] U.S. Cl. ................................... 351/203; 351/243; 351/244
[58] Field of Search .............................. 351/2, 32–37; 128/76.5

[56] References Cited

U.S. PATENT DOCUMENTS 2,089,863  8/1937  Updegrave .............................. 351/2
2,213,467  9/1940  Greenspoon .
3,875,934  4/1975  Sadanaga .

Primary Examiner—John K. Corbin
Assistant Examiner—Rodney B. Bovernick
Attorney, Agent, or Firm—McDermott, Will & Emery

[57] ABSTRACT

An optical testing and exercising device including a stereo film viewer having a pair of eyepieces and one or more lenses which can be interposed along the user's line of sight to change the apparent distance of an image. The viewer also includes a housing with a pair of juxtaposed eyepieces and an opening to receive a film having a series of frames bearing images to be viewed. A frame advancing mechanism advances successive frames of the film into the line of sight of the device for viewing by the user through the juxtaposed eyepieces. The frame advancing mechanism also changes one or more lenses mounted in the housing between the eyepieces and the film receiving opening into the viewer's line of sight. The interposed lenses can be utilized for various effects, such as to change the apparent distance of the image from the viewer, thus causing the eye muscles to be exercised. Various combinations of lenses and images can be used with the device to test for many types of vision functions such as suppression, accommodation, acuity, phoria, and color vision.

15 Claims, 7 Drawing Figures

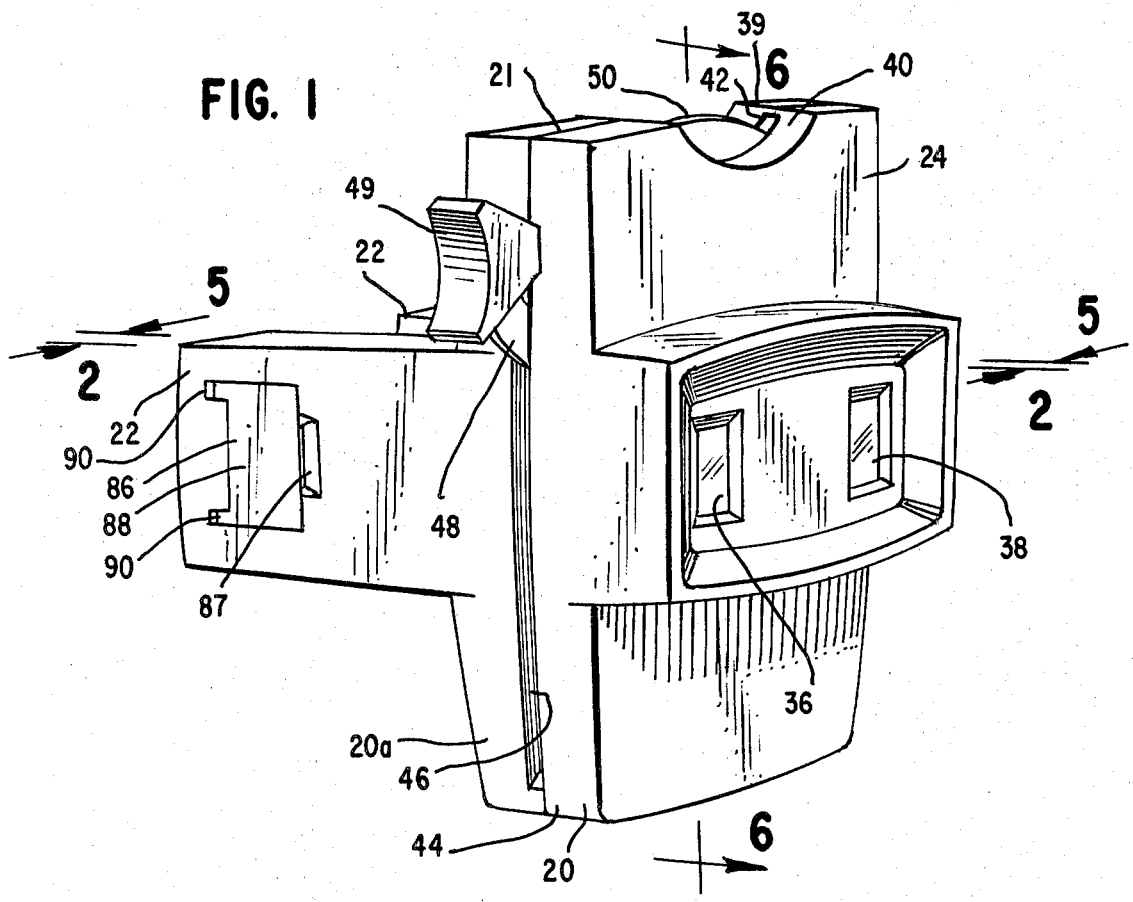
FIG. 1
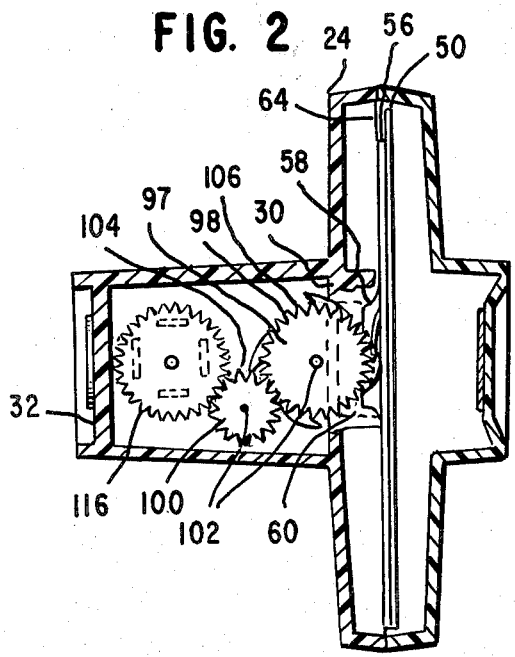
FIG. 2
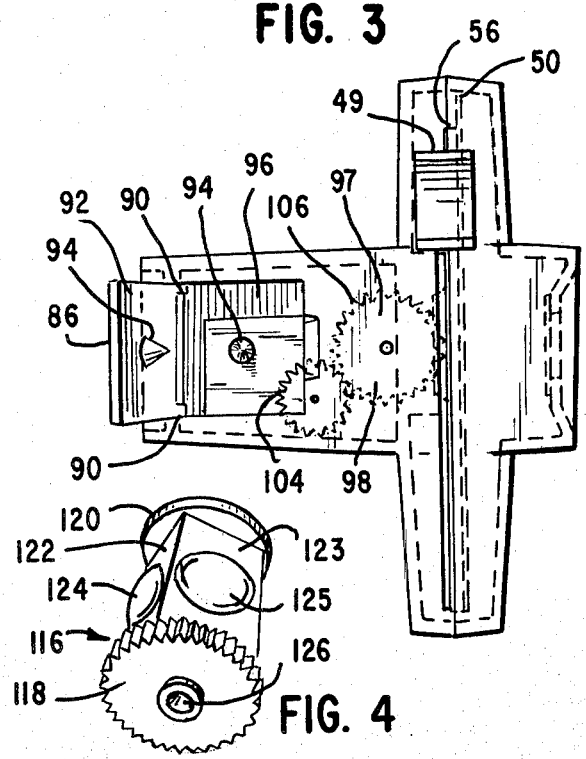
FIG. 3
FIG. 4

OPTICAL EXERCISING DEVICE

BACKGROUND OF THE INVENTION

1. Field of the Invention

This invention relates generally to eye exercising devices and more particularly to portable eye exercising devices useful for correcting accommodation and convergence deficiencies of the human eye.

2. Prior Art

Binoculars-like eye training devices which force the user's eyes to accommodate for an actual or apparent change in the location of an image held by the device in the user's line of sight are known. For example U.S. Pat. No. 3,875,934 issued to Sadanaga discloses a device which reciprocates a pair of lenses along the viewer's line of sight and U.S. Pat. No. 2,213,467 issued to Greenspoon discloses a device in which a card is reciprocated toward and away from the viewer.

The prior art devices require that the user repetitively move the actual or apparent location of the image viewed toward and away from him along his line of vision so that the ocular muscles are exercised in the process. This tends to be very boring and users are inclined not to undertake the treatment which has been prescribed. This difficulty can be overcome by requiring that the treatment be undertaken in the doctor's office; however, this would result in considerable expense and inconvenience to the patient. Thus there is a need for an orthoptic training device which encourages continued adherence to the prescribed treatment regimen. This is particularly so in the case of devices for young children.

SUMMARY OF THE INVENTION

Accordingly, it is an object of the present invention to provide an improved orthoptic training device that overcomes the disadvantages of the prior art.

It is another object in the present invention to provide a portable and inexpensive device which can be used by the patient at the patient's leisure in the home.

It is still another object of the present invention to provide an orthoptic training device which encourages the user to adhere to the training program.

It is a further object of the present invention to provide an eye testing and training device which is not now available.

In accordance with one form of the preferred embodiment of the present invention an eye testing and exercising device is provided which includes a housing with a pair of juxtaposed openings and a means for mounting a film having a series of frames bearing images to be viewed. The device also includes a set of interchangeable eyepieces and a frame advancing mechanism for advancing successive frames of the film to be viewed before the openings. The frame advancing mechanism is operatively connected to at least two movably mounted lenses mounted in the housing between the film mounting means and the eyepieces in order to move the lenses. As successive frames of the film are viewed the apparent distance of the image from the person viewing the image may be changed or other desired effects may be created.

BRIEF DESCRIPTION OF THE DRAWINGS

These and other objects and advantages of the present invention will be more readily understood upon consideration of the detailed description and attached drawings wherein:

FIG. 1 is a perspective view of an embodiment of the present invention:

FIG. 2 is a reduced cross-sectional view taken generally along the line 2—2 in FIG. 1;

FIG. 3 is a reduced side elevational view of the embodiment of the present invention shown in FIG. 1;

FIG. 4 is a perspective view of a rotating lens cartridge used in conjunction with the present invention;

DETAILED DESCRIPTION OF THE PREFERRED EMBODIMENT

Figure 5:
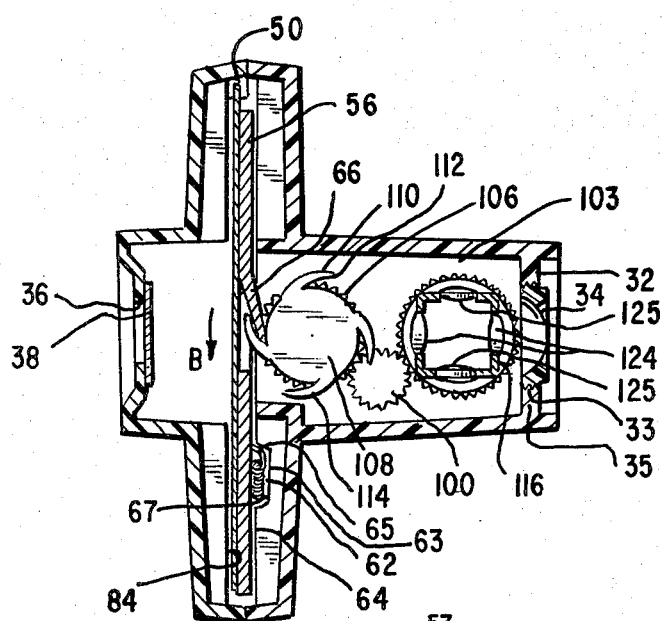
FIG. 5 is a reduced cross-sectional view taken generally along the line 5—5 in FIG. 1.

Referring to the drawings, wherein like reference characters are used for like parts throughout the several views there is shown in FIG. 1 a binoculars-like eye exercising device 20. The device 20 includes a pair of juxtaposed viewing barrels 22, a film retaining housing portion 24 situated at the end of the viewing barrels 22 and a pair of light admitting apertures 36. The device 20 can be conveniently made of two molded pieces 20a and 20b joined along the line 21 by suitable means not shown.

As shown in FIG. 5, each barrel 22 includes an open end 30 which connects to film retaining housing 24 and an end 32 which is closed and opaque to light except for a centrally positioned eyepiece 34. The end 32 may conveniently be removably secured within barrel 22 by threaded fasteners 33 which thread through end 32 into tabs 35 extending from the interior walls of barrel 22. The eyepiece 34 is removably mounted in the end 32 to permit changing of the eyepieces to effect various alterations in the image to be viewed.

Along the optical axis of each eyepiece 34 on the opposite side of film retaining housing 24 there is positioned a light admitting aperture 36. Preferably the light admitting aperture 36 contains a translucent plate 38 which admits diffused ambient light to suitably illuminate the image to be viewed.

As shown in FIGS. 1 and 2, the film retaining housing portion 24 extends perpendicularly above and below the viewing barrels 22. The uppermost edge 39 of housing 24 includes a dished out portion 40 and a central slot 42. In addition, one side 44 includes a generally vertically extending, centrally positioned slot 46. A lever 48 extends out of the slot 46 from the interior housing 24. A finger engaging tab 49 is secured to the end of the lever 48.

Figure 6:
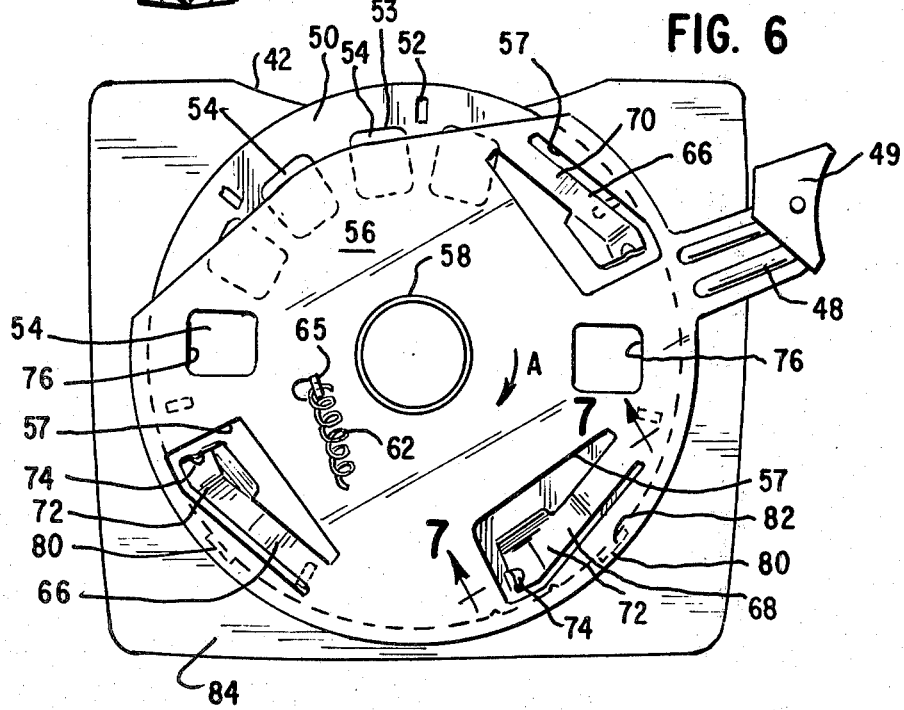
FIG. 6 is a partial, reduced cross-sectional view taken generally along the line 6—6 in FIG. 1.

As shown in FIG. 6, central slot 42 and the interior of housing 24 are adapted to receive a circular slide plate 50. The slide plate 50 includes a plurality of side by side translucent film slides 54 secured within openings 53 arranged around and spaced slightly from its periphery. The plates 50, widely available in consumer outlets, are sold by the GAF Corporation of Portland, Oregon under the trademark VIEWMASTER. In addition to the side by side slides 54, often bearing cartoon scenes, the plates 50 also have a plurality of peripherally arranged, equally spaced slots 52. When the slides are advanced one by one into the viewer's light of sight a cartoon or story sequence is revealed to the user.

Mounted within the housing 24 is a rotatable frame advancing mechanism 56. The frame advancing mechanism 56 is generally a substantially circular flat plate having an outwardly extending central ring 58 which rotatably telescopes within a tubular portion 60 formed in the inside wall 64 of housing 24. The frame advancing mechanism 56 is rotated by pressing downwardly on the film advancing lever 48 which extends outwardly of housing 24 and is connected to film advancing mechanism 56. The advancing mechanism 56 rotates in the direction indicated by arrow A in response to actuation of the lever 48. However the rotation of the mechanism 56 is resisted by return spring 62 which lies in a depression 63 in inside wall 64 of housing 24, secured between a pin 67 extending out from inside wall 64 and a pin 65 on mechanism 56. Thus, when the force upon the lever 48 is released the spring causes the frame advancing mechanism to return to its original position.

The circular slide plate 50 is retained in position in housing 24 by a pair of outwardly extending pins 80 which jut out from the inside wall 64 of housing 24. Each pin 80 has a surface 82 which is shaped to conform to the curvature of the slide plate 50. Thus the slide plate 50 is wedged by its own weight between the surfaces 82 of pins 80. The slide plate 50 is also held snugly between the opposite inside wall 84 and the frame advancing mechanism 56 which lies flush against the inside wall 64.

Figure 7:
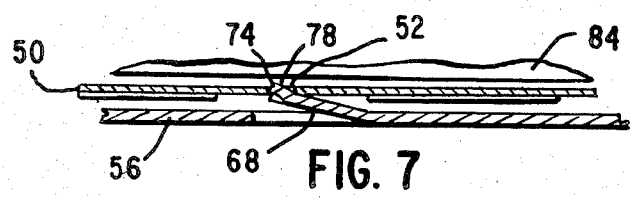
FIG. 7 is an enlarged cross-sectional view taken generally along the line 7—7 of FIG. 6.

Extending out of the plane of frame advancing mechanism 56 but secured thereto are a pair of rearwardly extending cams 66 and a forwardly extending cam 68. Each cam 66 or 68 includes a generally circumferentially aligned spring arm 70 which extends slightly out of the plane of the mechanism 56 and connects to the mechanism 56 near its periphery within an opening 57. The cams 66 extend out of the plane of mechanism 56 toward inside wall 64 while cam 68 extends in the opposite direction toward inside wall 84. Attached to the unconnected end of the arm 70 is a widened flange 72 having a hump 74 formed therein. The mechanism 56 is conveniently made of flexible metal sheeting by metal stamping or the like. As shown in FIG. 7, hump 74 on forwardly extending arm 68 engages a peripherally spaced slot 52 in circular slide plate 50 when the frame advancing mechanism 56 is rotated causing the circular slide plate to be rotated in the direction indicated by the arrow A. The extent of possible movement of the lever 48, governed by the length of slot 46 or other suitable detent means, is such that each time the lever is operated the next slide to be viewed is precisely positioned within windows 76 of frame advancing mechanism 56. By making the slides 54 which appear in each viewing window 76 left and right stereoscopic images an illusion of depth perception can be achieved.

When the film frame advancing lever 48 is released and the frame advancing mechanism rotates back to its original position the circular slide plate 50 does not move because of the camming action of the inclined surface 78 of hump 74 on forwardly extending cam 68. The surface 78 is pressed into the plane of frame advancing mechanism 56 against its own natural spring bias so that the circular slide plate 50 is not moved. When the film frame advancing lever 48 returns to its upward, normal position, the raised tab 74 again slides into a mating slot 52 in circular slide plate 50.

Each of the viewing barrels 22 has an access door 86, only one of which is visible in FIG. 1, on its outward facing side 88. The access door 86 is mounted for rotation on two spaced hinges 90 from the closed position shown in FIG. 1 to the open position shown in FIG. 3. Conveniently the door is frictionally maintained in its closed position and opened by inserting a finger in depression 87. As shown in FIG. 3, on the inside surface 92 of door 86 is a centrally mounted conical aligning tab 94. When the door 86 is closed, the aligning tab 94 faces an identical tab 94 pointing in the opposite direction and located on the interior surface of opposite wall 96 of each viewing barrel 22.

Also contained within each viewing barrel 22 is a dual surfaced cam gear 98 and a mating gear 100, shown in FIG. 2. The cam gear 98 and the mating gear 100 are each mounted on the inside surface 103 of outward facing side 88 of barrel 22 by means of a pair of inwardly extending pins 102 attached to the inside surface 103 of side 88. The mating gear 100 has a plurality of gear teeth 104 which intermesh with the teeth 106 on geared cylindrical portion 97 of cam gear 98. Mounted for conjoint rotation with the portion 97 is a coaxially mounted, cylindrical cam portion 108, shown in FIG. 5, having four equally spaced, circumferentially arranged outwardly extending cam members 110. Each cam member 110 has a hook-shaped engaging surface 112 and an opposed hump-shaped camming surface 114.

An interchangeable, removable, rotating lens cartridge 116, shown in FIG. 4, includes a gear disc 118, a circular plate 120 and two pairs of opposed, parallel lens carrying plates 122 and 123 which extend between and connect gear disc 118 and circular plate 120. The plates 122 are oriented at 90° from plates 123 to form a rectangular array. Each of the plates 122 or 123 may carry a centrally positioned generally coplanar lens 124 or 125 which may conveniently be circular in shape. The gear disc 118 and the circular plate 120 each has a centrally positioned conically shaped indentation 126 (only one of which is shown) on their outwardly facing sides, shaped to mate with centrally mounted conical aligning tabs 94 on the walls of viewing barrel 22. Thus a cartridge 116 can be inserted into each barrel 22 by inserting the tab 94 on opposite wall 96 into the indentation 126 of circular plate 120 and by closing the access door 86 so that tab 94 on access door 86 slides into the indentation 126 on gear disc 118 centering the rotating lens cartridge 116 on the two aligning tabs 94, for rotation thereon between walls 88 and 96 of a barrel 22. In this position, as shown in FIG. 2, the gear disc 118 of lens cartridge 116 engages the teeth 104 of mating gear 100 so that rotation of cam gear 98 causes opposite rotation of mating gear 100 and rotation in the same direction of rotating lens cartridge 116.

Referring now to FIG. 5, one of the rearwardly extending cams 66 of frame advancing mechanism 56 is shown in engagement with the hook-shaped engaging surface 112 of a cam member 110 on cam portion 108 of cam gear 98. Movement of a rearwardly extending cam 66 past the cam member 110 causes cam gear 98 to rotate. Since the teeth 106 of the geared cylindrical portion 97 of cam gear 98 are in engagement with teeth 104 of mating gear 100 the rotation of the cam gear 98 is transmitted to mating gear 100. The rotation of mating gear 100 is then transmitted to rotating lens cartridge 116. As shown in FIG. 6 there is one rearwardly extending cam 66 for each viewing barrel 22, one moving downwardly in response to actuation of frame advancing lever 48 and the other moving upwardly in response to the same actuation.

The device operates as follows. The user first slides a circular slide plate 50 into central slot 42 of dished out portion 40 pressing the slide plate 50 into the slot until the lower edge of the slide plate 50 comes to rest against the outwardly extending pins 80. The region between the frame advancing mechanism 56 and the inside wall 84 of film retaining housing 24 is small enough that the slide plate 50 is held firmly against frame advancing mechanism 56. The user then positions each eye before one of the centrally positioned eyepieces 34 in each viewing barrel 22 and peers into the device. The viewer's line of sight as shown in FIG. 5 includes in addition to the eyepieces 34, two pairs of lenses 124, a diametrically opposed pair of slides 54 of circular slide plate 50 and a pair of translucent plates 38. Ambient light shines through translucent plate 38 illuminating each slide 54 in the line of sight. As the user views one slide with each eye, if the slides are stereoscopic left and right images, the appearance of depth will be perceived. The lenses 124 of rotating lens cartridge 116 are ground to a power value which makes the image appear relatively near or far from the user.

To view the next slide in the series of slides, the user presses downwardly on frame advancing lever 48 causing rotatable frame advancing mechanism 56 to rotate as indicated by the arrow A together with circular slide plate 50 which is pressed flush against the mechanism 56. This rotation is due to the engagement of hump 74 of forwardly extending cam 68 with a peripherally spaced slot 52 in the circular slide plate 50. When the frame advancing lever 48 reaches its downwardmost extension the lever 48 is released and returns automatically to its normal upward position due to the action of return spring 62. However, circular slide plate 50 does not rotate back with the frame advancing mechanism because forwardly extending cam 68 is biased inwardly into the plane of frame advancing mechanism 56 due to the action of cam shaped reverse surface 78 of the cam 68. In this way the left and right images contained on slides 54 are positioned in windows 76 of frame advancing mechanism 56. It should be clear that the next slide 54 in the series will not be the one adjacent the slides just viewed but, in fact, will be spaced some distance therefrom. However, the slides can be arranged around the circular slide plate 50 so that they will all eventually be viewed.

Simultaneously with the rotation of frame advancing mechanism 56 and circular slide plate 50, a rotating lens cartridge 116 in each barrel 22 is rotated 90° to position the other pair of lenses 125 in the line of sight of the user. This is accomplished by the action of the rearwardly extending cams 66 each of which engages a cam member 110 on a cam gear 98 causing gear rotation in the direction of the applied force indicated by arrow B in FIG. 5. The rotation of cam gear 98 results in the rotation of mating gear 100 in turn rotating the intermeshing gear disc 118 of cartridge 116. The number of teeth on the gears and the size of the gears is such that the downward movement of the frame advancing lever 48 exactly advances the next pair of lenses into the line of sight of the viewer. Since the gears 98 and 100 are mounted for rotation close to the inside surface 103 of outwardly facing side 88 of viewing barrel 22 the gears are not in the line of sight of the viewer. Because the two opposed pairs of lenses 124 and 125 are ground to different power values, the imposition of the set of lenses 125 in the line of sight causes the image to appear at a different distance than it appeared with the prior set of lenses 124. Although the cartridges 116 in each barrel are rotated in different directions, the 90° rotation is effective to impose lenses 125 in the line of sight in each barrel.

Thus the viewer's eye muscles are exercised by forcing them to diverge and/or converge to the apparent change in direction of the image being perceived. In this way each time the next successive slide is advanced into the user's line of vision the rotating lens cartridge 116 will be concurrently rotated 90° causing the apparent distance of the image to be changed. Thus the viewer will be induced to undertake the needed eye training in the course of viewing successive slides. Since the viewer will naturally desire to view the entire slide sequence, the viewer will be inclined to submit to the needed training, quite possibly without any noticeable annoyance since the lens change occurs as the slide is changed.

In addition to this training and exercising function, the present invention is readily usable as a testing apparatus. For example, the device would be particularly useful as a school screening tool to test for acuity, suppression, phoria, color blindness and many other types of vision abnormalities. Simple construction of required stereo image combinations or series of combinations could replace the conventional "eye chart" or "color vision charts". Additionally, suppression could be checked in a similar manner by providing stereo images of three separate indicia or rows of indicia having a common or overlapping element which is visible to both eyes while the other two elements are visible only to one of the eyes. In a test for blocking function, alternate lenses on the removable cartridge 116 could be opaque requiring the user to use only one eye or alternately use his eyes.

The rotation of cam gear 98 results in a 90° rotation of its cam portion 108 causing another cam member 110 to rotate into position to be subsequently engaged by a cm 66 when lever 48 is again actuated. The cam member 110 newly rotated into position is not rotated by the reverse rotation of frame advancing mechanism 56 caused by return spring 62. This is because the opposed hump-shaped camming surface 114 of cam member 110 flexes the cam 66 inwardly into the plane of mechanism 56, on its return path, by engaging the inclined surface 78 of hump 74 of cam 66. The cam 66 slides over cam member 110 and stops with its hump 74 aligned with and ready to engage the hook-shaped engaging surface 112 of member 110 when the mechanism 56 is again activated.

Because the eyepieces 34 and rotating lens cartridge 116 are removable from the device, different lens systems can be used depending on the particular patient's condition and the degree of exercise which is appropriate at the time. Thus either the user or his physician may maintain a library of eyepieces 34 and rotating lens cartridges 116 which can be plugged into the exercising device 20, all containing lenses of different lens and prism power values. If desired the hatch door 86 can have a catch (not shown) which makes it difficult for the user to remove the rotating cartridge 116 and thereby avoid the prescribed treatment.

With the end 32 of each viewing barrel 22 being removable, different ends 32 having different eyepieces 34 may be secured within each barrel 22. Then eyepieces of different power value can be positioned along the line of sight to create desired visual environments. For example, a far viewing distance or a close viewing distance lens can be positioned in the end 32 of viewing barrel 22 so that the rotating lens cartridge 116 then creates various accommodation demands relative to these viewing distances.

If desired, a four position indexing gear, with four equally spaced, peripheral depressions, engaged by a resilient leaf spring mounted on the inside surface 103 of side 88, can also be coaxially positioned on the outwardly extending pin 102 upon which cam gear 98 is mounted. This will insure that the proper alignment and synchronization of the rotating lens cartridge 116 is always maintained.

In still another alternative embodiment the hatch door 86 may have a small window near its upper edge to enable the user or his physician to view the outward facing surface of the gear disc 118. The outward facing surface of the gear disc 118 having printed indicia which identify the lens system in use will then be visible through the window. The close proximity of the gear disc 118 to the window will prevent light from entering the barrel 22 which would obscure the slide being viewed.

The device can also be used to test for suppression, color blindness or other vision problems by using a pair of slides which detect a specific problem, one of which is interposed before each barrel 22. For example, in suppression, the slides viewed by each eye each have two letters, one of which is common to the two slides. The common letter is positioned on the right of the slide viewed by the left eye and on the left of the slide viewed by the right eye so that normally the user will see three letters, the common letter on each slide appearing once in the middle of the image. If either of the outer two letters is not perceived suppression can be diagnosed.

Since many modifications and variations of the present invention are possible in light of the above teachings, for example, using a translating rather than a rotating slide advance mechanism, or translating a lens along the viewer's line of sight to change the apparent distance of the image instead of rotating a lens into and out of the line of sight, it is to be understood that, within the scope of the appended claims the invention may be practiced otherwise than as specifically described above.

What is claimed and desired to be secured by Letters Patent of the United States is:

1. An eye testing/training device, comprising:
   a housing;
   a pair of side by side viewing openings in said housing;
   means for mounting in said housing in the line of sight of said openings a film having a series of frames bearing images to be viewed;
   a frame advancing mechanism for advancing successive frames to be viewed before said openings;
   at least one movably mounted lens in said housing generally between said film mounting means and said openings; and
   means operatively connecting said frame advancing mechanism to said movably mounted lens for moving said lens resulting in a change in the characteristics of the image to the user.

2. The orthoptic device of claim 1 having a pair of juxtaposed viewing barrels and a means for interposing a left stereoscopic film frame before one barrel and a right stereoscopic film frame before the other barrel.

3. The orthoptic device of claim 2 having a rotating frame advancing mechanism and cam members attached to said mechanism which engage said film to index successive frames of said film before said openings.

4. The orthoptic device of claim 3 wherein said frame advancing mechanism is a flat plate having a lever extending outwardly thereof, said plate adapted to engage a circular slide plate bearing a plurality of frames arranged around its periphery.

5. The orthoptic device of claim 1 wherein said lens is removably mounted in said housing.

6. The orthoptic device of claim 1 wherein said lens is mounted on at least one support, said support mounted for rotation within said housing to move said lens into and out of the line of sight of said openings.

7. The orthoptic device of claim 6 having two pairs of lenses mounted on said support one pair before each opening, one of said lens of said pair before each opening having a different power value than the other to make the image viewed appear to be at different distances depending on which lenses are in the line of sight.

8. The orthoptic device of claim 6 or 7 including a gear train operated by said frame advancing mechanism to rotate said support as the frame is advanced.

9. The orthoptic device of claim 6 said device being a portable stereo viewer having a removable eyepiece in each of said openings and means for mounting stereoscopic left and right slide frames before said eyepieces.

10. The orthoptic device of claim 1 or 9 including image means on said film in said film mounting means for detecting eye abnormalities.

11. An improvement in an eye testing stereoviewer having a frame advancing mechanism for advancing successive frames to form an image to be viewed through an eyepiece, said improvement comprising:
    at least one movably mounted lens between the image and the eyepiece; and
    means operatively connecting said frame advancing mechanism to said movably mounted lens for moving said lens resulting in a change in the characteristics of the image to the user.

12. The eye testing device of claim 11 having a pair of juxtaposed viewing barrels and a means for interposing a left stereoscopic film frame before one barrel and a right stereoscopic film frame before the other barrel.

13. The eye testing device of claim 12 having a rotating frame advancing mechanism and cam members attached to said mechanism which engage said film to index successive frames of said film before the eyepieces.

14. The eye testing device of claim 11 wherein sid lens is removably mounted in said housing.

15. An eye testing device comprising:
    a stereoviewer;
    compatible means for supporting a plurality of film frames for sequential viewing in said stereoviewer;
    a plurality of paired indicia on said film frames for detecting vision abnormalities of the user; and
    at least one movably mounted lens interposed in front of said compatible means; and
    means operatively connecting said compatible means to said movably mounted lens for moving said lens resulting in a change in the characteristics of the frames viewed through said lens by the user.

* * * * *